US008987526B2

(12) United States Patent
Kokubo et al.

(10) Patent No.: US 8,987,526 B2
(45) Date of Patent: Mar. 24, 2015

(54) PARTIALLY HALOGENATED, HYDROXYLATED FULLERENE AND ALLERGEN ADSORBENT USING THE SAME

(71) Applicants: Osaka University, Suita-Shi, Osaka (JP); Totai Co., Ltd., Tokyo (JP)

(72) Inventors: Ken Kokubo, Suita (JP); Takeshi Noguchi, Yofu (JP)

(73) Assignees: Osaka University, Osaka (JP); Totai Co., Ltd., Tokyo (JP)

( * ) Notice: Subject to any disclaimer, the term of this patent is extended or adjusted under 35 U.S.C. 154(b) by 0 days.

(21) Appl. No.: 14/495,438

(22) Filed: Sep. 24, 2014

(65) Prior Publication Data

US 2015/0011802 A1    Jan. 8, 2015

Related U.S. Application Data

(62) Division of application No. 13/577,868, filed as application No. PCT/JP2011/051864 on Jan. 31, 2011.

(30) Foreign Application Priority Data

Feb. 8, 2010 (JP) ................................ 2010-025303

(51) Int. Cl.

| C07C 35/23 | (2006.01) |
|---|---|
| B01J 20/22 | (2006.01) |
| C01B 31/02 | (2006.01) |
| C07C 17/02 | (2006.01) |
| C07C 25/22 | (2006.01) |
| C07C 35/52 | (2006.01) |
| C07C 29/48 | (2006.01) |
| C07C 29/62 | (2006.01) |
| C07C 29/124 | (2006.01) |
| B82Y 30/00 | (2011.01) |
| B82Y 40/00 | (2011.01) |

(52) U.S. Cl.
CPC ............ *B01J 20/22* (2013.01); *C01B 31/0213* (2013.01); *C07C 17/02* (2013.01); *C07C 25/22* (2013.01); *C07C 35/52* (2013.01); *C07C 2104/00* (2013.01); *C07C 29/48* (2013.01); *C07C 29/62* (2013.01); *C07C 29/124* (2013.01); *B82Y 30/00* (2013.01); *B82Y 40/00* (2013.01); *Y10S 977/734* (2013.01); *Y10S 977/736* (2013.01); *Y10S 977/74* (2013.01); *Y10S 977/735* (2013.01)
USPC ........... 568/817; 977/734; 977/736; 977/740; 977/735

(58) Field of Classification Search
CPC .. C07C 2104/00; C07C 29/62; Y10S 977/734
USPC ................... 977/734, 735, 736, 740
See application file for complete search history.

(56) References Cited

U.S. PATENT DOCUMENTS

| 7,371,479 B2 | 5/2008 | Nuber |
| 7,695,706 B2 | 4/2010 | Nuber |
| 2007/0145352 A1* | 6/2007 | Kasama et al. ................ 257/40 |

FOREIGN PATENT DOCUMENTS

| JP | 7-48302 A | 2/1995 |
| JP | 2000-5531 A | 1/2000 |
| JP | 2002-167332 A | 6/2002 |
| JP | 2002-193861 A | 7/2002 |
| JP | 2004-204401 A | 7/2004 |
| JP | 2005-104907 A | 4/2005 |
| JP | 2007-254246 A | 10/2007 |
| JP | 2008-94656 A | 4/2008 |
| JP | 2008-280290 A | 11/2008 |
| WO | 2008/096763 A1 | 8/2008 |

OTHER PUBLICATIONS

Zope et al., "Static dielectric response of icosahedral fullerenes from C60 to C2160 by an all electron density functional theory", Phys. Rev. B., 77, 115452—(2008), 6 pages, with 2 page abstract.
Ala'A K. Abdul-Sada, et al., "Isolation and characterisation of fluorinated derivatives of [76]- and [78]fullerenes," J. Chem. Soc., Perkin Trans. 2, pp. 2659-2666 (1999).
Anthony G. Avent, et al., "In the first proven SN2' fullerene reaction, both C3 and Cl C60F36 hydrolyse to Cl isomers of C60F35OH that eliminate HF to give epoxides C60F36O oxides are shown to be ethers, and a fourth isomer of C60F36 exists," Org. Biomol. Chem., 1, pp. 1026-1033 (2003).
Paul R. Birkett, et al., "Preparation and 13C NMR Spectroscopic Characterisation of C60Cl6," J. Chem. Soc., Chem. Commun., pp. 1230-1232 (1993).
Long Y. Chiang, et al., "Efficient Synthesis of Polyhydroxylated Fullerene Derivatives via Hydrolysis of Polycyclosulfated Precursors," J. Org. Chem., 59, pp. 3960-3968 (1994).
Ken Kokubo, et al., "Facile Synthesis of Highly Water-Soluble Fullerences More Than Half-Covered by Hydroxyl Groups," American Chemical Society, vol. 2, No. 2, pp. 327-333 (2008).
Fred N. Tebbe, et al., "Multiple, Reversible Chlorination of C60," J. Am. Chem. Soc. 113, pp. 9900-9901 (1991).
Fred N. Tebbe, et al., "Synthesis and Single-Crystal X-ray Structure of a Highly Symmetrical C60 Derivative, C60Br24," Science, vol. 256, pp. 822-825 (May 8, 1992).

(Continued)

*Primary Examiner* — Fereydoun G Sajjadi
*Assistant Examiner* — Pancham Bakshi
(74) *Attorney, Agent, or Firm* — Rothwell, Figg, Ernst & Manbeck, P.C.

(57) ABSTRACT

Provided are a novel fullerene derivative which can adsorb quickly and efficiently an allergen which may cause a pollen allergy without releasing the allergen again, does not contain a metal or the like which may cause a harmful effect to a human body, and is easily applicable, impregnable, or chemically bondable onto surface of various materials: and a process for producing the same. The fullerene derivative is characterized in that a halogen group and many hydroxyl groups are bonded directly to a fullerene nucleus. In the case that the halogen group is chlorine, the fullerene derivative can be synthesized by a partial hydroxylation of a chlorinated fullerene or a partial chlorination of a hydroxylated fullerene.

2 Claims, 7 Drawing Sheets

(56) References Cited

OTHER PUBLICATIONS

Pavel A. Troshin, et al., "Synthesis of Fullerenols from Halofullerenes," Fullerenes, Nanotubes, and Carbon Nanostructures, 13, ISSN 1536-383X print/1536-4046 online, pp. 331-343 (2005).
Sergey I. Troyanov, et al., "Synthesis and Structures of Fullerene Bromides and Chlorides," Eur. J. Org. Chem., pp. 4951-4962 (2005).
Sergei I. Troyanov, et al., "Two Isomers of C60F48: An Indented Fullerene," Angew. Chem. Int. Ed., 40, No. 12, pp. 2285-2287 (2001).
Sheng Wang, et al., "Novel and Efficient Synthesis of Water-Soluble [60]Fullerenol by Solvent-Free Reaction," Synthetic Communications, 35, pp. 1803-1808 (2005).
Jiang; Tetrahedron; 2008, 64, 11394-11403.

* cited by examiner

PARTIALLY HALOGENATED, HYDROXYLATED FULLERENE AND ALLERGEN ADSORBENT USING THE SAME

CROSS REFERENCE TO RELATED APPLICATIONS

This application is a divisional of U.S. application Ser. No. 13/577,868, filed Oct. 9, 2012, which is a 35 U.S.C. §371 National Phase Entry Application from PCT/JP2011/051864, filed Jan. 31, 2011, and designating the United States, which claims benefit of Japanese Patent Application No. 2010-025303 filed on Feb. 8, 2010, all of which are incorporated herein by reference in their entireties all purposes.

TECHNICAL FIELD TO WHICH THE INVENTION RELATES

The present invention relates to a fullerene derivative which can adsorb an allergen quickly; and a method for producing the same.

BACKGROUND ART

It is estimated that number of the pollen allergy patients in this nation approaches about 20% of the entire people; however, the present situation is that a fundamental mean for cure the disease has not been established yet in spite of such a large number. Under such situation, a symptomatic therapy and a hyposensitization therapy are used as the medical care for the disease, wherein wearing of a mask and use of an air cleaner are still major effective means as cheap and convenient countermeasures for the pollen. The situation like this seems much the same in rest of the world.

In the past, it has been proposed to use a material or a substance having a function to adsorb or inactivate a pollen and an allergen in a mask and a filter product. For example, in Japanese Patent Application Laid-Open No. 2000-5531 (Patent Document 1), a tea polyphenol is proposed as a substance to inactivate an allergic activity of an allergen substance. In Japanese Patent Application Laid-Open No. 2002-167332 (Patent Document 2), it is disclosed to adsorb an allergen by a non-woven fabric to which an inorganic microparticle such as silica and titanium oxide is supported. In Japanese Patent Application Laid-Open No. 2004-204401 (Patent Document 3), a pollen-adsorbing material using a polymer fiber having a positively-charged functional group such as a quaternary ammonium salt is proposed.

As mentioned above, various countermeasures have been investigated in the past; however, with the aims not only to continuously improve its removing effect but also to be effective on a wide variety of allergen, bacteria, or virus, development of a totally new type of an allergen adsorbent is desired.

PRIOR ART

Patent Document

[Patent Document 1]: Japanese Patent Application Laid-Open No. 2000-5531
[Patent Document 2]: Japanese Patent Application Laid-Open No. 2002-167332
[Patent document 3]: Japanese Patent Application Laid-Open No. 2004-204401

DISCLOSURE OF THE INVENTION

Problems to be Solved by the Invention

In view of the above-described current situation, it is an object of the present invention to provide an adsorbent which can adsorb in a short time and efficiently an allergen causing a pollen allergy without releasing the allergen again and which does not contain a metal or the like causing a harmful effect to a human body.

In addition, it is another object of the present invention to provide a novel fullerene derivative easily applicable, impregnable, or chemically bondable onto surface of various materials.

It is a further object of the present invention to provide a method for producing the adsorbent or the fullerene derivative as mentioned above.

Means to Solve the Problems

According to the present invention, the foregoing objects are achieved by a fullerene derivative characterized in that the fullerene derivative has both a hydroxyl group and a halogen group.

The present invention accomplished the foregoing objects by a fullerene derivative characterized in that the fullerene derivative has both a hydroxyl group and a halogen group bonded directly to a fullerene nucleus thereof and is shown by the general formula of $CpXn(OH)m$ (wherein p represents an even number of 60 or more, X represents a halogen group, n represents a number of more than 0 (not including 0) and 48 or less, and m represents a number of more than 0 (not including 0) and 44 or less).

In this case, the halogen group is not particularly restricted; but it is preferred that the halogen group is chlorine, bromine, and fluorine or preferable.

As to the fullerene as the starting raw material, $C_{60}$ or $C_{70}$, or a mixture of $C_{60}$ with a fullerene of $C_{70}$ or a higher may be used.

In addition, the present invention accomplished the foregoing objects by a method for producing a fullerene derivative characterized in that bonding of a hydroxyl group to a fullerene nucleus of a halogenated fullerene having a halogen group bonded to the fullerene nucleus is made such that a part of the halogen groups still remain, thereby producing a partially halogenated, hydroxylated fullerene.

In the case of a chlorinated fullerene having chlorine as the halogen group, a partially chlorinated, hydroxylated fullerene may be produced by reacting the chlorinated fullerene with hydrogen peroxide, sodium hydroxide, or potassium hydroxide.

A partially brominated, hydroxylated fullerene may be produced by reacting a brominated fullerene having bromine as the halogen group with sodium hydroxide or potassium hydroxide.

Further, the present invention accomplished the above-mentioned objects by a method for producing a fullerene derivative characterized in that bonding of a halogen group to a fullerene nucleus of a hydroxylated fullerene having a hydroxyl group bonded to the fullerene nucleus is made such that a part of the hydroxyl groups still remains, thereby producing a partially halogenated, hydroxylated fullerene.

In addition, the present invention accomplished the above-mentioned objects by a method for producing a fullerene derivative characterized in that bonding of a chlorine to a fullerene nucleus of a hydroxylated fullerene having a hydroxyl group bonded to the fullerene nucleus is made by reacting the hydroxylated fullerene with iodine chloride such that a part of the hydroxyl groups still remains, thereby producing a partially chlorinated, hydroxylated fullerene.

According to the present invention, an allergen adsorbent containing the above-mentioned fullerene derivative is provided.

Advantages of the Invention

The fullerene derivative of the present invention has a hydroxyl group and a halogen group directly bonded to a fullerene nucleus thereof and does not contain a metal or the like which may cause a harmful effect to a human body.

In addition, the fullerene derivative of the present invention can efficiently and quickly adsorb an allergen which may cause a pollen allergy, and moreover, does not release the allergen once adsorbed again. That is, a protein like an allergen has many amino groups and carboxyl groups thereby easily interacting chemically with a highly polar functional group such as a hydroxyl group and a halogen group so that an allergen can be adsorbed efficiently and quickly.

Meanwhile, based on an extensive investigation by the inventors of the present invention, they assumed that a fullerene needs to have a hydrophilic surface because a protein such as an allergen has a hydrophilic functional group; and thus, study was made on a hydroxylated fullerene (fullerene derivative having only a hydroxyl group bonded), but a satisfactory result could not be obtained therefrom. By making a fullerene derivative to have both a hydroxyl group and a halogen group, which is the derivative of the present invention, a satisfactory result on adsorption of an allergen was obtained.

According to the present invention, because a fullerene derivative is a spherical carbon molecule having a nanometer size, surface area thereof can be made large; and thus, it is suitable for an adsorbent. In other words, because particle diameter and surface area of an adsorbent is in an inversely proportional relationship provided that weights thereof are the same, if particle diameter becomes smaller, surface area for adsorption becomes larger; and thus, the fullerene derivative of the present invention is suitable as the adsorbent.

The fullerene derivative of the present invention has both a hydroxyl group and a halogen group concurrently, and thus it has an amphipathic property of both hydrophilicity and hydrophobicity. Because of this, the fullerene derivative of the present invention can be applied to, impregnated with, or chemically bonded to surface of various materials.

The fullerene derivative of the present invention can be used as an adsorbent of an allergen, a substance to cause a pollen allergy (in the case of a cedar pollen, a protein coded as Cry j1 is a main substance); and thus, it can be applied to a mask having high effect to remove a pollen and to a filter of an air cleaner.

According to the present invention, a novel fullerene derivative having both many hydroxyl and halogen groups concurrently can be produced by a comparatively convenient method. That is, this fullerene derivative can be synthesized by partial hydroxylation of a halogenated fullerene or by partial halogenation of a hydroxylated fullerene.

THE BEST MODES FOR CARRYING OUT THE INVENTION

Figure 1:
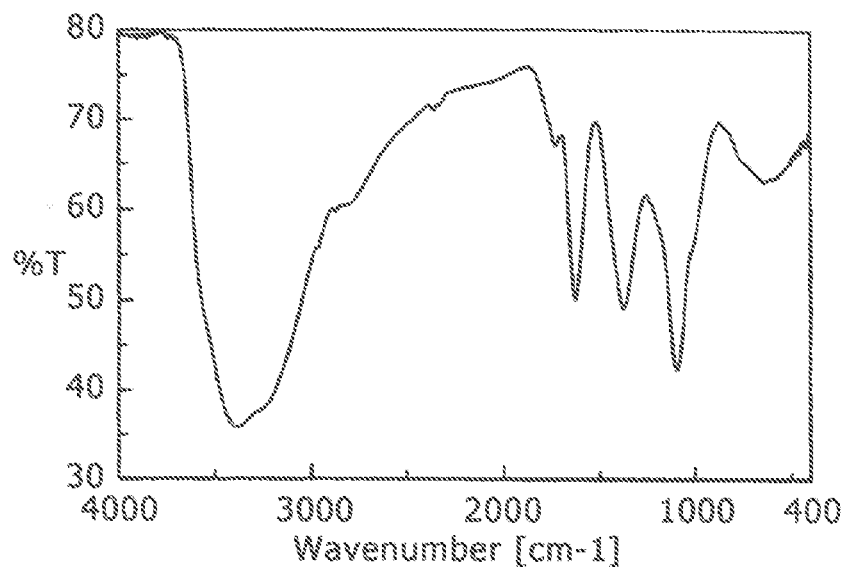
FIG. 1 is an infrared absorption spectrum chart of water-soluble hydroxylated fullerene $C_{60}(OH)_{44} \cdot 8H_2O$ by a Fourier-transformed infrared spectroscopy (FT-IR) wherein transmittance is shown in a vertical axis and wavenumber is shown in a horizontal axis.

Hereinafter, the present invention will be explained in detail.

The novel fullerene derivative of the present invention has a halogen group as well as a hydroxyl group in a fullerene nucleus thereof.

More specifically, provided is a fullerene derivative shown by the general formula of CpXn(OH)m (wherein p represents an even number of 60 or more, X represents a halogen group, n represents a number of more than 0 and 48 or less, and m represents a number of more than 0 and 44 or less).

Meanwhile, the fullerene derivative of the present invention may contain or not contain secondary bound water. When number of the hydroxyl group is small, there is no secondary bound water contained therein, while secondary bound water is prone to be contained therein as number of the hydroxyl group increases.

There is no particular restriction in the fullerene to produce the fullerene derivative of the present invention provided that the fullerene is a spherical carbon molecule; but $C_{60}$, or $C_{70}$, or a mixture of $C_{60}$ with a fullerene of $C_{70}$ or higher (for example, $C_{76}$, $C_{78}$, $C_{80}$, $C_{84}$, $C_{86}$, and so on) is preferable. Fullerenes used in Examples are $C_{60}$; however it is not restricted to fullerene $C_{60}$, it is expected that a compound having a structure as well as a property similar to those of the foregoing fullerenes may be obtained, even if, fullerene $C_{70}$, which has similar chemical and physical properties to fullerene $C_{60}$, or a mixed fullerene containing $C_{60}$ (a mixture of $C_{60}$, $C_{70}$, and a higher fullerene), is used as the starting raw material thereof.

It is preferred that the halogen group (X) in the present invention is fluorine (F), chlorine (Cl), and bromine (Br), among monovalent elements belonging to the group 7B of the periodic table.

The fullerene derivative of the present invention is produced by partial hydroxylation or partial halogenation due to hydroxylation (or hydrolysis) of a halogenated fullerene or halogenation (or a halogen-substitution reaction) of a hydroxylated fullerene. When a substitution reaction is used, the reaction is carried out till about midway of the reaction (namely, partial hydroxylation or partial halogenation). When purely only an addition reaction is carried out, theoretically the reaction may be carried out until completion of the reaction.

Hydroxylation of a halogenated fullerene is mainly carried out by a substitution reaction; and thus, the reaction is carried out until the state where a part of the halogen groups remains (this can be controlled by reaction conditions, time, equivalence of reagents, and the like). In addition, during the time of hydroxylation of a halogenated fullerene, in some cases, an addition reaction of the hydroxyl group may occur simultaneously, and secondary bound water may be included therein.

Halogenation of a hydroxylated fullerene is effected mainly by an addition reaction; but according to Examples, if number of the hydroxyl groups in the hydroxylated fullerene as the starting raw material of the reaction is large, number of the hydroxyl groups in the product after the reaction is decreased, and it is suggested that introduction of the halogen group is effected by a substitution reaction.

The halogenated fullerene or the hydroxylated fullerene, which is the starting raw materials of the fullerene derivative of the present invention, has already been known.

For example, a chlorinated fullerene $C_{60}Cl_n$ is obtained by chlorinating fullerene $C_{60}$ as a starting raw material; and production methods thereof have already been known in the following Non-Patent Documents 1 to 3.

[Non-Patent Document 1]: J. Am. Chem. Soc., 1991, 113, 9900
[Non-Patent Document 2]: J. Chem. Soc., Chem. Commun., 1993, 1230
[Non-Patent Document 3]: Eur. J. Org. Chem., 2005, 4951

Methods for producing a fluorinated fullerene, a chlorinated fullerene, and a brominated fullerene are disclosed in the following Patent Document 4.

[Patent Document 4]: Japanese Patent Application Laid-Open No. 2002-193861

In the following Non-Patent Document 4, method for producing a fluorinated fullerene $C_{60}F_{48}$ is disclosed.

[Non-Patent Document 4]: Angew. Chem. Int. Ed., 2001, 40, 2285

In the following Non-Patent Document 5, method for producing a brominated fullerene $C_{60}Br_{16}$ is disclosed.

[Non-Patent Document 5]: Science, 1992, 256, 822

Meanwhile, in the method for producing the fullerene derivative of the present invention, a halogenated fullerene which is a starting raw material thereof and which is produced by any method may be used.

A hydroxylated fullerene $C_{60}(OH)_m$ is obtained by hydroxylation of fullerene $C_{60}$ as a starting raw material, and production methods thereof have already been known. For example, it can be produced by the methods disclosed in the following documents.

[Patent Document 5]: Japanese Patent Application Laid-Open No. H07-48302
[Patent Document 6]: International Patent Publication No. WO2008/096763
[Non-Patent Document 6]: J. Org. Chem., 1994, 59, 3960
[Non-Patent Document 7]: Synth. Commun., 2005, 35, 1803
[Non-Patent Document 8]: ACS Nano, 2008, 2, 37

Meanwhile, in the method for producing the fullerene derivative of the present invention, a hydroxylated fullerene which is a starting raw material and which is produced by any method may be used.

In addition, a method to substitute all the halogen groups of a halogenated fullerene with hydroxyl groups is disclosed in the following documents.

[Patent Document 4]: Japanese Patent Application Laid-Open No. 2002-193861
[Non-Patent Document 9]; Fullerenes, Nanotubes, and Carbon Nanostructures, 2005, 13, 331

As mentioned above, a halogenated fullerenes and hydroxylated fullerenes have been conventionally known; but a partially halogenated, hydroxylated fullerene having both the halogen group and the hydroxyl group, like the fullerene derivative of the present invention, has not been known until now.

In the case that the halogen group is chlorine, the fullerene derivative of the present invention may be synthesized by partial hydroxylation of a chlorinated fullerene (method A) or partial chlorination of a hydroxylated fullerene (method B), after fullerene is converted to the chlorinated fullerene or the hydroxylated fullerene, or by using a known chlorinated fullerene or hydroxylated fullerene. For example, in the case that fullerene is $C_{60}$, the methods are shown as the following [Chem. 1].

[Chem. 1]

In the case that a chlorinated fullerene is partially hydroxylated (method A), number "n" of the chlorine groups introduced is the same as the number "n'" of the chlorine substituent groups of the chlorinated fullerene which is a starting raw material, or is decreased due to the substitution reaction to the hydroxyl group. As to the method of the partial hydroxylation, there are a general hydrolysis reaction using a basic catalyst such as sodium hydroxide or potassium hydroxide and a hydroxylation reaction using an aqueous hydrogen peroxide; but the method is not limited to these methods. For example, as to the hydroxylating reagent for this partial hydroxylation, in addition to sodium hydroxide and potassium hydroxide, LiOH, RbOH, CsOH, Ca(OH)$_2$, Sr(OH)$_2$, Ba(OH)$_2$, TlOH, nBuN(OH), Triton B, and so on may be applicable.

In the case that a hydroxylated fullerene is partially chlorinated (method B), number "m" of the hydroxyl groups introduced may be the same as the number "m'" of the substituent groups of the hydroxylated fullerene which is a starting raw material, or may be decreased due to the substitution reaction to the chlorine group, or may be increased due to operation during reaction work-up. As to the method of the partial chlorination, a chlorination reaction using iodine chloride (ICl) is shown in Examples; but the reagent thereof is not limited to this reagent. For example, POCl$_3$, PCl$_5$, SbCl$_5$, VCl$_4$, VOCl$_3$, MoCl$_5$, and KICl$_4$, in addition to iodine chloride, may be applicable as a reagent.

Solvents usable in production of a starting raw material of the present invention (halogenated fullerene or hydroxylated fullerene) and in hydroxylation of a halogenated fullerene or in halogenation of a hydroxylated fullerene may be; for example, an aromatic solvent such as o-dichlorobenzene, chlorobenzene, trimethylbenzene, xylene, toluene, and benzene;

a halogenated solvent such as methylene chloride, chloroform, carbon tetrachloride, dichloroethane, and tetrachloroethane;

a non-protonic polar solvent such as THF, ether, ethyl acetate, dioxane, DMF, and DMSO; and other solvents such as carbon disulfide and acetonitrile.

Although there is no particular restriction regarding the numbers "n" and "m" in [Chem. 1] described above, "n" and "m" as long as they are at least larger than 0, "n" is smaller than the maximum number 30 which is known in $C_{60}Cl_{n'}$ (see, the above-described Non-Patent Document 3), and "m" is smaller than the maximum number 44 which is known in $C_{60}(OH)_{m'}$ (see, the above-described Patent Document 5). In addition, these numbers may be an inherent number assigned to one isomer or an average number of a mixture of many isomers. Further, the introduction positions of these substituents on surface of the fullerene nucleus are not particularly restricted.

In the case that the halogen group is bromine or fluorine, partial hydroxylation may be carried out, similarly to [Chem. 1] described above, by a general hydrolysis reaction of a brominated fullerene or a fluorinated fullerene by using a basic catalyst such as sodium hydroxide and potassium hydroxide, or by a hydroxylation reaction using an aqueous hydrogen peroxide.

In this case too, number "n" of the bromine or the fluorine substituent groups in the synthesized fullerene derivative is the same as the number "n'" of the substituent groups of the starting raw material, or is decreased due to the substitution reaction to the hydroxyl group. As to the brominated fullerene or the fluorinated fullerene which is used as the starting raw materials, having many substituent groups, $C_{60}F_{48}$ is known as disclosed in the above-described Non-Patent Document 4 and Patent Document 4; and thus, number of the halogen substituent groups "n" in the fullerene derivative of the present invention is 48 or less at its maximum.

In the synthetic method of the present invention, even if, not only fullerene $C_{60}$, but also fullerene $C_{70}$ or a mixed fullerene containing $C_{60}$ (a mixture of $C_{60}$, $C_{70}$, and a higher fullerene), which has similar chemical and physical properties to fullerene $C_{60}$, is used as the starting raw material thereof, it is expected that a compound having a structure as well as a property similar to those of the foregoing fullerenes may be obtained.

The present invention will be explained hereinbelow with reference to Examples, but the present invention is no way limited by these Examples.

Example 1

Synthesis of Hydroxylated Fullerene $C_{60}(OH)_{44}\cdot 8H_2O$

Synthesis of this was done by the method disclosed in Patent Document 6. Namely, 100 mg of $C_{60}$ (commercial product with the trade name of "nanom purple" manufactured by Frontier Carbon Corp.) was dissolved into 50 mL of toluene, and into it were added 5 mL of 30% aqueous hydrogen peroxide and tetra(n-butyl) ammonium hydroxide (40% aqueous solution, 500 µL) as a phase-transfer catalyst; and then, the resulting mixture was stirred at 60° C. for 16 hours. From this solution, a toluene layer that became colorless was removed. The aqueous layer after removal of the toluene layer was gradually added into 85 mL of a mixed solution of hexane, diethyl ether, and 2-propanol with the ratio of 5:5:7 under irradiation with an ultrasonic wave to precipitate a pale yellow solid. The formed precipitate was sedimented by centrifugal separation, and then, a supernatant solution therein was removed by decantation. This solid was washed with 60 mL of diethyl ether and then sedimented again; and then, after a supernatant solution was removed therefrom, the solid was dried under vacuum at room temperature overnight. By doing so, a crude reaction product of a hydroxylated fullerene was obtained as pale yellow powders.

To remove the catalyst remained therein, this solid was dissolved into 3 mL of water and the resulting solution was passed through a column for chromatography packed with about 1 g of Florisil (60 to 100 mesh) and with about 6 cm length. The aqueous solution after removal of the catalyst was passed through a membrane filter with 0.45 µm to completely remove Florisil as well. Into this aqueous solution were added hexane, diethyl ether, and 2-propanol with the ratio to water volume being 5:5:7 to precipitate a pale yellow solid. This solid was dried under vacuum at room temperature overnight to obtain a purified product of a hydroxylated fullerene $C_{60}(OH)_{44}\cdot 8H_2O$ as pale yellow powders (yield of 149 mg and 67%). Infrared absorption spectrum (IR) of the product thus obtained is shown in FIG. 1.

Synthesis of Partially Chlorinated, Hydroxylated Fullerene $C_{60}Cl_{10}(OH)_{30}\cdot 5H_2O$ Into 2.5 mL of tetrahydrofurane (THF) was well dispersed 200 mg of $C_{60}(OH)_{44}\cdot 8H_2O$ obtained in accordance with the method described above with irradiating an ultrasonic wave for 5 minutes, and then, 0.5 mL of ICl was added thereinto; the reaction thereof was carried out at room temperature (rt) for 2.5 hours ([Chem. 2] described below). After confirming that the solid was disappeared whereby changing to a clear, reddish brown solution, THF and ICl were removed by distillation by using an evaporator under reduced pressure. Further, in order to remove iodine that was by-produced and contained therein as a black-purple solid, washing thereof by using hexane was repeated for about 20 times; and when color of the filtrate thereof became a light red color, a brown solid was collected by centrifugal separation and then dried under vacuum at room temperature overnight (yield of 208 mg and 100%).

[Chem. 2]

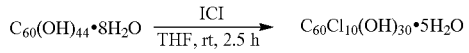

$$C_{60}(OH)_{44}\cdot 8H_2O \xrightarrow[\text{THF, rt, 2.5 h}]{\text{ICl}} C_{60}Cl_{10}(OH)_{30}\cdot 5H_2O$$

Figure 2:
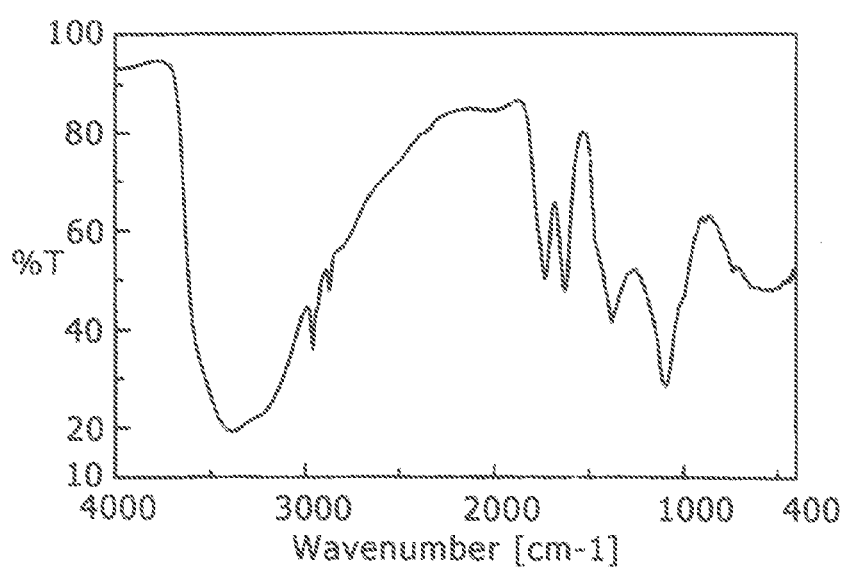
FIG. 2 is a FT-IR spectrum chart of partially chlorinated, hydroxylated fullerene $C_{60}Cl_{10}(OH)_{30} \cdot 5H_2O$.

Infrared absorption spectrum (IR) of the product thus obtained as mentioned above is shown in FIG. 2. The IR spectrum shown in FIG. 2 is somewhat different from the spectrum (shown in FIG. 1) of hydroxylated fullerene $C_{60}(OH)_{44}\cdot 8H_2O$ which was used as the starting raw material thereof, suggesting that the reaction took place, while remaining characteristics of the hydroxylated fullerene spectrum (not only a large and broad absorption peak near 3400 cm$^{-1}$ assignable to O—H stretching of the hydroxyl group but also broad absorption peaks near 1620, 1380, and 1080 cm$^{-1}$ assignable to C—C and C—O stretching). In addition, weight loss of 5.0 wt % was observed while heating from room temperature to around 100° C. in a thermogravimetric analysis of this product. This weight loss was estimated as amount of the secondary bound water contained in the product. Values of the elemental analysis thereof were: 41.870 for C, 3.00% for H, and 21.84% for Cl; and these values coincided well with the calculated values for $C_{60}Cl_{10}(OH)_{30}\cdot 5H_2O$ (43.01% for C, 2.41% for H, 21.16° for Cl, and 5.4% by weight for $H_2O$).

Example 2

Synthesis of Partially Chlorinated, Hydroxylated Fullerene $C_{60}Cl_2(OH)_{38}\cdot 6H_2O$ Hydroxylated fullerene $C_{60}(OH)_{44}\cdot 8H_2O$ (200 mg) obtained by the method of Example 1 and 1 mL of ICl were reacted at room temperature for 24 hours (following [Chem. 3]). A black residue of highly viscous slurry was washed repeatedly with hexane for about 15 times and then dissolved into methanol; and thereafter, methanol was removed by distillation under reduced pressure by using an evaporator. The resulting brown solid thus obtained was added into ethanol, and then dispersed well by irradiation with an ultrasonic wave; and thereafter, hexane was added thereinto. A yellow solid precipitated therein was collected by centrifugal separation, washed with diethyl ether, and then dried under vacuum at room temperature overnight (yield of 120 mg and 63%).

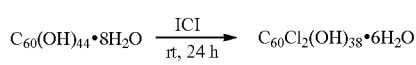
[Chem. 3]

Figure 3:
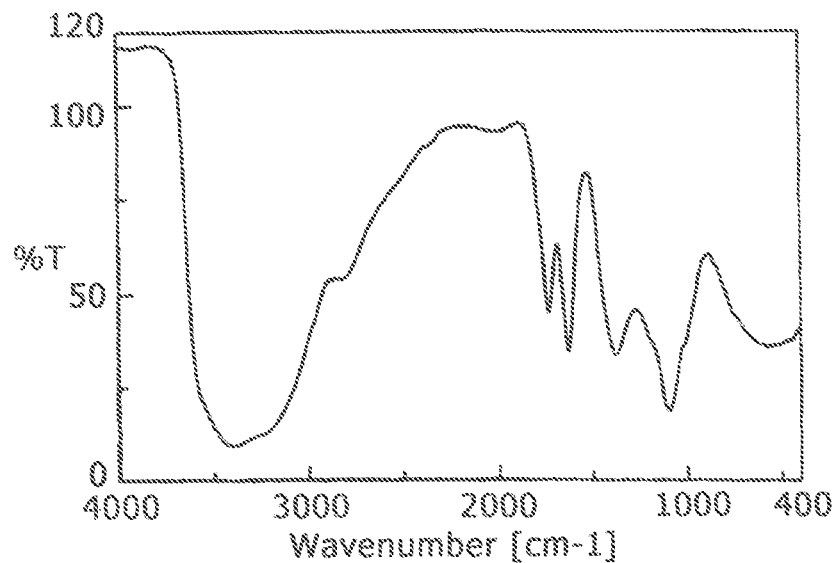
FIG. 3 is a FT-IR spectrum chart of partially chlorinated, hydroxylated fullerene $C_{60}Cl_2(OH)_{38} \cdot 6H_2O$.

IR spectrum of the product thus obtained is shown in FIG. 3. The IR spectrum shown in FIG. 3 is somewhat different from the IR spectrum shown in FIG. 1 of hydroxylated fullerene $C_{60}(OH)_{44} \cdot 8H_2O$ which was used as the starting raw material thereof, suggesting that the reaction took place, while remaining characteristics of the hydroxylated fullerene spectrum. In addition, according to a thermogravimetric analysis of this product, weight loss of 7.4 wt % was observed while heating from room temperature to around 120° C. This weight loss was estimated as amount of the secondary bound water contained in the product. Values of the elemental analysis thereof were: 46.73% for C, 2.56% for H, and 4.76% for Cl; and these values coincided well with the calculated values for $C_{60}Cl_2(OH)_{38} \cdot 6H_2O$ (46.61% for C, 3.26% for H, 4.59% for Cl, and 7.0% by weight for $H_2O$).

Example 3

Synthesis of Hydroxylated Fullerene $C_{60}(OH)_{12} \cdot 5H_2O$

Figure 4:
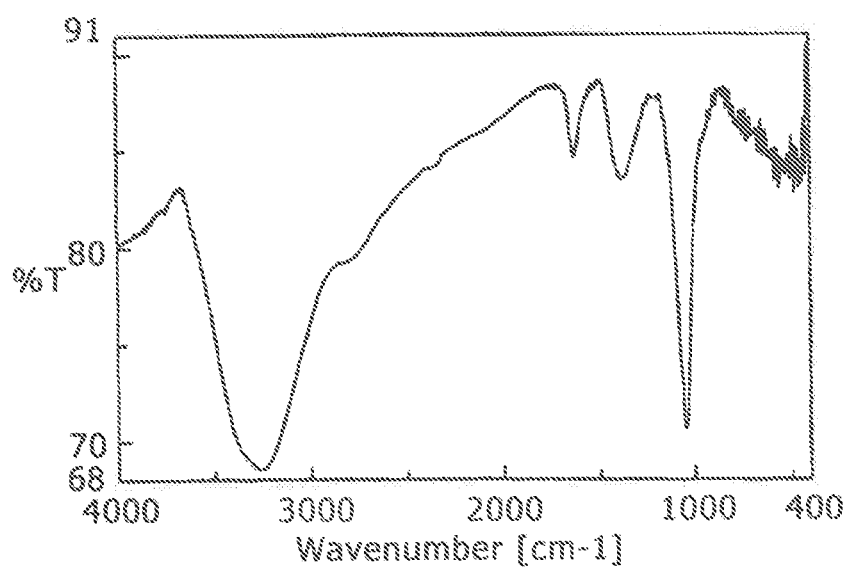
FIG. 4 is a FT-IR spectrum chart of hydroxylated fullerene $OH(OH)_{12} \cdot 5H_2O$.

This was synthesized by the method disclosed in Non-Patent Document 6. Namely, 10 g of $C_{60}$ and 150 mL of 60% fuming sulfuric acid were stirred under nitrogen atmosphere at a temperature of between 55 and 60° C. for 3 days. The reaction mixture thereby obtained was gradually added with vigorous stirring into diethyl ether kept in an ice bath; and then, a precipitated product was separated by centrifugal separation. The precipitated product thus obtained was washed with diethyl ether, separated by centrifugal separation, washed further with a mixed solvent of diethyl ether and acetonitrile, separated by centrifugal separation, and then dried at 40° C. under vacuum, and 13 g of polycyclosulfated fullerene was obtained as reddish orange powders. This polycyclosulfated fullerene (5.0 g) and 100 mL of distilled water were stirred under nitrogen atmosphere at 85° C. for 10 hours, and then, a precipitated product thus formed was separated by centrifugal separation. The obtained precipitated product was washed with water, separated by centrifugal separation, then dried at 40° C. under vacuum, and hydroxylated fullerene $C_{60}(OH)_{12} \cdot 5H_2O$ obtained as brownish-red powders (yield of 4.5 g). IR spectrum of the product thus obtained is shown in FIG. 4.

Synthesis of Partially Chlorinated, Hydroxylated Fullerene $C_{60}Cl_{15}(OH)_{15} \cdot 9H_2O$ $C_{60}(OH)_{12} \cdot 5H_2O$ (100 mg) obtained by the method described above and 1 mL of ICl were reacted at room temperature for 24 hours (see [Chem. 4] described below). A black residue of highly viscous slurry was washed repeatedly with hexane for about 15 times, added with THF, and then dispersed well by irradiation with an ultrasonic wave; and thereafter, hexane was added thereinto. A yellow solid precipitated out by addition of hexane was collected by centrifugal separation, and then dried under vacuum at room temperature overnight (yield of 117 mg and 71%).

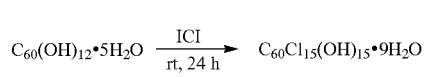
[Chem. 4]

Figure 5:
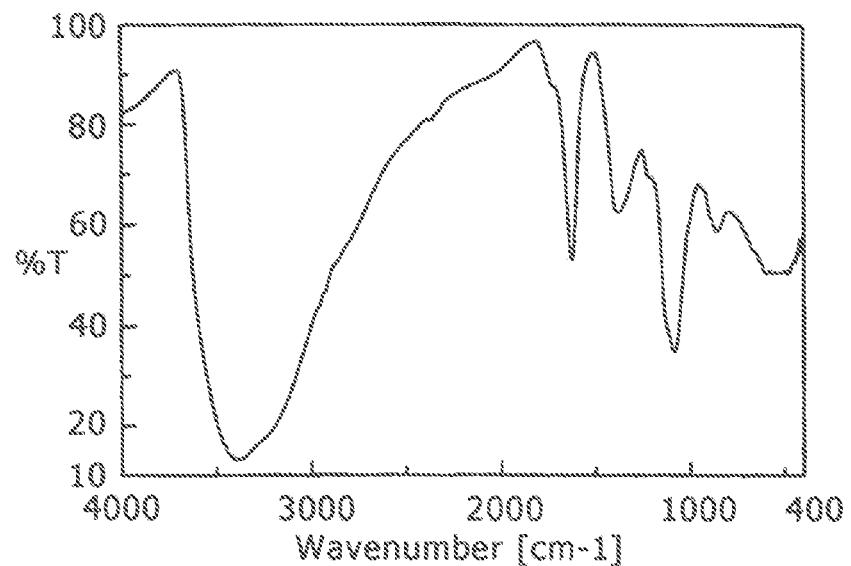
FIG. 5 is a FT-IR spectrum chart of partially chlorinated, hydroxylated fullerene $C_{60}Cl_{15}(OH)_{15} \cdot 9H_2O$.

IR spectrum of this product is shown in FIG. 5. The IR spectrum shown in FIG. 5 is somewhat different from the IR spectrum (see FIG. 4) of hydroxylated fullerene $C_{60}(OH)_{12} \cdot 5H_2O$ which was used as the starting raw material thereof, suggesting that the reaction took place, while remaining characteristics of the hydroxylated fullerene spectrum. In addition, in a thermogravimetric analysis thereof, weight loss of 9.7 wt % was observed while heating from room temperature to around 110° C.; and thus, this weight loss was estimated as amount of the secondary bound water contained in the product. Values of the elemental analysis thereof were: 42.68% for C, 1.60% for H, and 32.57% for Cl; and these values coincided well with the calculated values for $C_{60}Cl_{15}(OH)_{15} \cdot 9H_2O$ (42.68% for C, 1.99% for H, 31.85% for Cl, and 9.7% by weight for $H_2O$).

Example 4

Synthesis of Partially Chlorinated, Hydroxylated Fullerene $C_{60}Cl_5(OH)_{15} \cdot 5H_2O$ Hydroxylated fullerene $C_{60}(OH)_{12} \cdot 5H_2O$ (100 mg) obtained by the method of Example 3 was dispersed well into 2.5 mL of THF by irradiation with an ultrasonic wave for 5 minutes, and then, 0.5 mL of ICl was added thereinto; and thereafter, the reaction thereof was carried out at room temperature for 24 hours (see [Chem. 5] described below). After completion of the reaction, THF and iodine were distilled out under reduced pressure. The resulting residue was washed repeatedly with hexane for about 10 times, added with ethyl acetate, and then dispersed well by irradiation with an ultrasonic wave. An orange-colored solid thus obtained was washed by addition of hexane for three times with irradiation of an ultrasonic wave. Thereafter, the orange-colored solid was collected by centrifugal separation, and then dried under vacuum at room temperature overnight (yield of 123 mg and 100%).

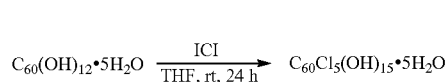
[Chem. 5]

Figure 6:
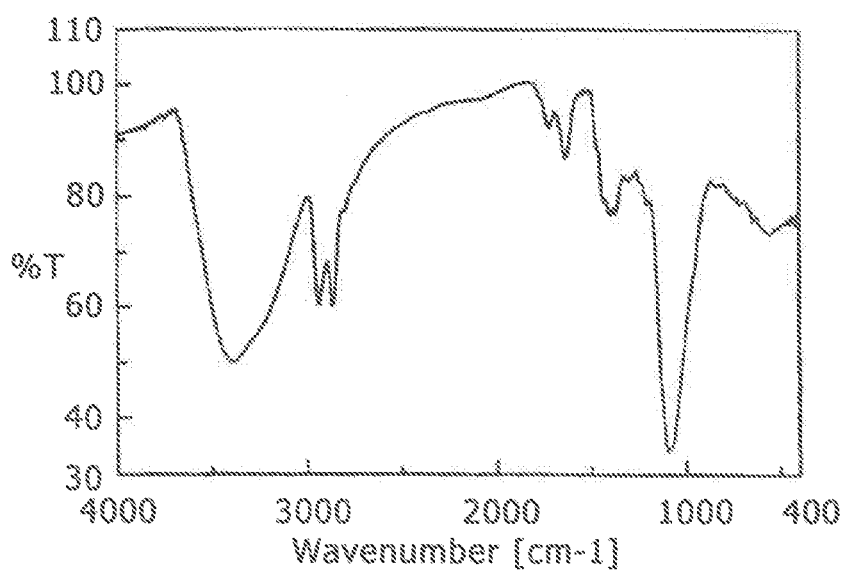
FIG. 6 is a FT-IR spectrum chart of partially chlorinated, hydroxylated fullerene $C_{60}Cl_5(OH)_{15} \cdot 5H_2O$.

IR spectrum of this product is shown in FIG. 6. The IR spectrum shown in FIG. 6 is somewhat different from the spectrum (see FIG. 4) of hydroxylated fullerene $C_{60}(OH)_{12} \cdot 5H_2O$ which was used as the starting raw material thereof, suggesting that the reaction took place, while remaining characteristics of the hydroxylated fullerene spectrum. In addition, according to a thermogravimetric analysis of the product, weight loss of 7.9 wt % was observed while heating from room temperature to around 110° C. This weight loss was estimated as amount of the secondary bound water contained in the product. Values of the elemental analysis thereof were: 58.89% for C, 3.86% for H, and 15.22% for Cl; and these values coincided well with the calculated values for $C_{60}Cl_5(OH)_{15} \cdot 5H_2O$ (57.97% for C, 2.03% for H, 14.26% for Cl, and 7.2% by weight for $H_2O$).

Example 5

Synthesis of Chlorinated Fullerene $C_{60}Cl_{28}$

This was synthesized by the method disclosed in Non-Patent Document 2. That is, into 60 mL of o-dichlorobenzene solution containing 2.33 g of $C_{60}$ was gradually added 20 mL of o-dichlorobenzene solution containing 7.5 g of ICl under an argon atmosphere; and then, the reaction was carried out at room temperature for 6 hours (see [Chem. 6] described below). After confirming completion of the reaction by a high performance liquid chromatography (HPLC), o-dichlorobenzene and by-produced iodine were distilled out by an evaporator. The resulting residue was washed with hexane; and then, a solid was collected by centrifugal separation; after washing it again with hexane, an orange-colored solid was collected by centrifugal separation. This was dried under vacuum at room temperature overnight (yield of 2.53 g and 78%).

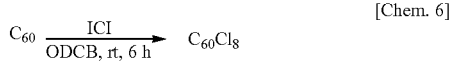

[Chem. 6]

Figure 7:
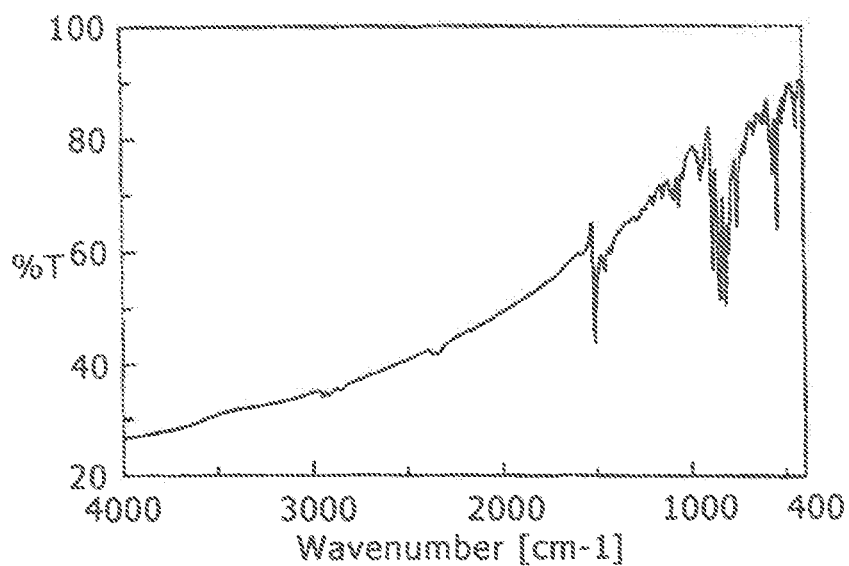
FIG. 7 is a FT-IR spectrum chart of chlorinated fullerene $C_{60}Cl_8$.

By measurement with a liquid chromatography-mass spectrometry (LCMS), a fragment peak of M=897, presumably corresponding to $C_{60}Cl_5$ (M=895), was obtained in a large peak of the product appeared as an almost single peak. IR spectrum of the product is shown in FIG. 7. IR spectrum of FIG. 7 resembles well with IR spectrum of the chlorinated fullerene $C_{60}Cl_6$ described in Non-Patent Document 2. Values of the elemental analysis thereof were: 72.53% for C and 28.24% for Cl; and these values coincided well with the calculated values for $C_{60}Cl_8$ (71.76% for C and 28.55% for Cl).

Synthesis of Partially Chlorinated, Hydroxylated Fullerene $C_{60}Cl_{0.5}(OH)_{35.5} \cdot 8H_2O$ $C_{60}Cl_8$ (1 g) obtained along the line described above was dissolved into 50 mL of 1,3,4-trimethylbenzene (TMB), and then reacted with 30 mL of 30% aqueous hydrogen peroxide ($H_2O_2$aq) in the presence of 5 mL of 40% aqueous solution of tetra(n-butyl) ammonium hydroxide (TBAH) as a phase transfer catalyst at 70° C. for 20 hours (see [Chem. 7] described above). After confirming that a red color of an organic upper layer was almost disappeared, an yellowish brown aqueous solution of a lower layer with amount of about 30 mL was collected. Into this were added 2-propanol, ethyl acetate, and hexane, respectively. A yellow solid precipitated out was collected by centrifugal separation and then dried under vacuum at room temperature overnight (yield of 980 mg and 66%).

[Chem. 7]

Figure 8:
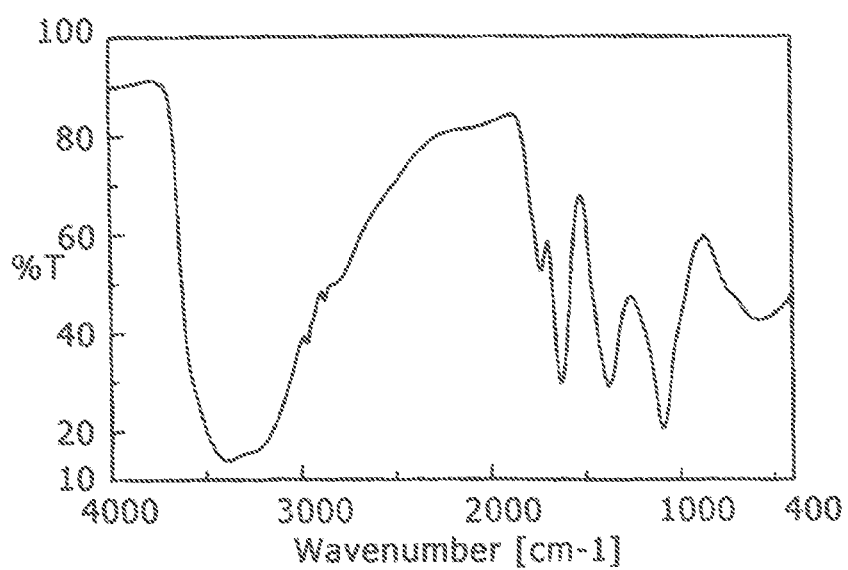
FIG. 8 is a FT-IR spectrum chart of partially chlorinated, hydroxylated fullerene $C_{60}Cl_{0.5}(OH)_{35.5} \cdot 8H_2O$.

IR spectrum of this product is shown in FIG. 8. The IR spectrum of FIG. 8 is significantly different from the IR spectrum (see FIG. 7) of chlorinated fullerene $C_{60}Cl_8$ which was used as the starting raw material thereof, suggesting that the reaction took place, while showing characteristics of the hydroxylated fullerene spectrum. In addition, in a thermogravimetric analysis thereof, weight loss of 9.8 wt % was observed while heating from room temperature to around 100° C. This weight loss was estimated as amount of the secondary bound water contained in the product. Values of the elemental analysis thereof were: 48.29% for C, 3.10% for H, and 1.06% for Cl; and these values coincided well with the calculated values for $C_{60}Cl_{0.5}(OH)_{35.5} \cdot 8H_2O$ (48.49% for C, 3.49% for H, 1.19% for Cl, and 9.7% by weight for $H_2O$).

Example 6

Synthesis of Chlorinated Fullerene $C_{60}Cl_{28}$

This was synthesized by the method disclosed in Non-Patent Document 3. That is, into 400 mg of $C_{60}$ was added 2 mL of ICl under an argon atmosphere; and then, the reaction was carried out at 120° C. for 40 hours (see [Chem. 8] described below). After completion of the reaction, black and purple crystals of iodine that were separated out in an upper part of the reactor was removed; and then, a brown solid thereby obtained was dried under vacuum at room temperature overnight (yield of 931 mg and 98%).

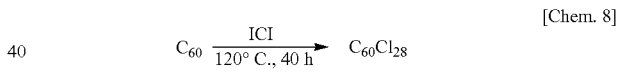

[Chem. 8]

Figure 9:
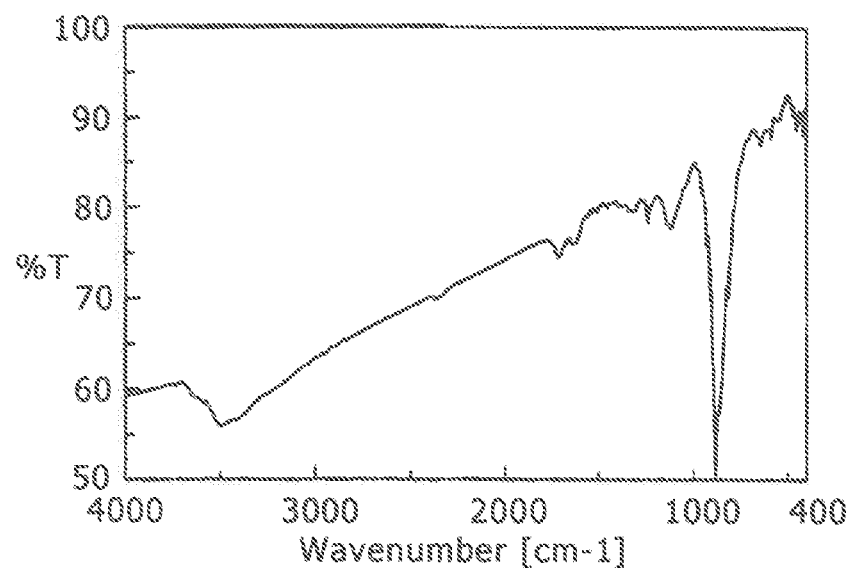
FIG. 9 is a FT-IR spectrum chart of chlorinated fullerene $C_{60}Cl_{28}$.

IR spectrum of this product is shown in FIG. 9. IR spectrum of FIG. 9 shows a large and broad C—Cl stretching and vibration peak at 883 cm$^{-1}$ and resembles well with the IR spectrum of chlorinated fullerene $C_{60}Cl_{28}$ described in Non-Patent Document 3. Values of the elemental analysis thereof were: 40.96% for C and 58.28% for Cl; and these values coincided well with the calculated values for $C_{60}Cl_{28}$ (42.06% for C and 57.94% for Cl).

Synthesis of Partially Chlorinated, Hydroxylated Fullerene $C_{60}Cl_3(OH)_{25} \cdot 6H_2O$ $C_{60}Cl_{28}$ (50 mg) obtained as described above was added with an aqueous sodium hydroxide (40.8 mM, 10 mL) that was prepared so as to be concentration of 14 equivalents relative to the fullerene nucleus therein, and then dispersed into water by irradiation with an ultrasonic wave; and then, the reaction was carried out at 60° C. for one hour (see [Chem. 9] described below). After confirming that the solution thereof became neutral by using a pH-test paper, a brown solid precipitated out by addition of methanol was collected by centrifugal separation, and then it was washed with ether. Thereafter, vacuum drying thereof was carried out at room temperature overnight (yield of 31.4 mg and 79%).

[Chem. 9]

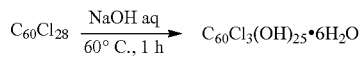

Figure 10:
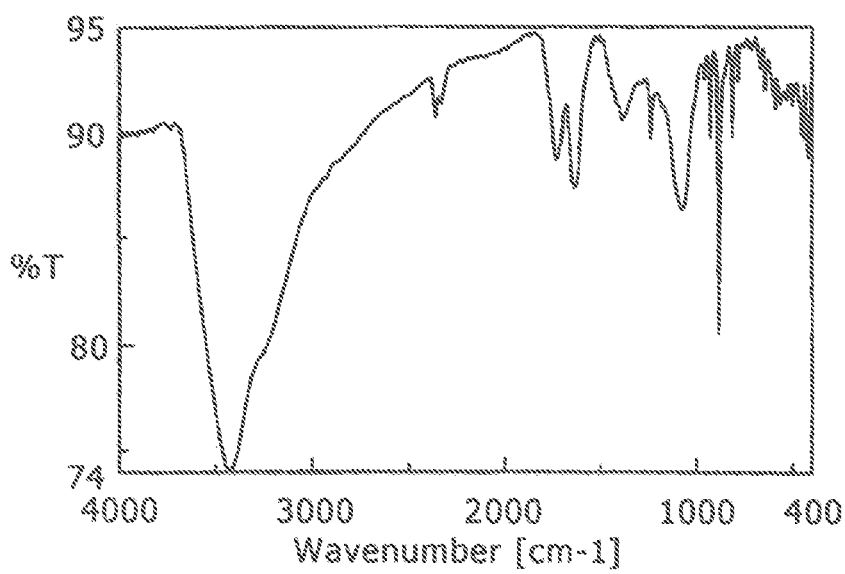
FIG. 10 is a FT-IR spectrum chart of partially chlorinated, hydroxylated fullerene $C_{60}Cl_3(OH)_{25} \cdot 6H_2O$.

IR spectrum of this product is shown in FIG. 10. The IR spectrum of FIG. 10 is significantly different from the spectrum (see FIG. 9) of chlorinated fullerene $C_{60}Cl_{28}$ which was used as the starting raw material thereof, suggesting that the reaction took place, and at the same time, showing spectrum characteristics of both of the hydroxylated fullerene and the chlorinated fullerene. In addition, in a thermogravimetric analysis thereof, weight loss of 8.2 wt % was observed while heating from room temperature to around 115° C., whereby this weight loss was estimated as amount of the secondary bound water contained in the product. Values of the elemental analysis thereof were: 53.57% for C, 2.49% for H, and 7.88% for Cl; and these values coincided well with the calculated values for $C_{60}Cl_3(OH)_{25} \cdot 6H_2O$ (52.98% for C, 2.74% for H, 7.82% for Cl, and 7.9% by weight for $H_2O$).

Example 7

Synthesis of Brominated Fullerene $C_{60}Br_{16}$

This was synthesized by the method disclosed in Non-Patent Document 5. That is, into 700 mg of $C_{60}$ was added 12 mL of $Br_2$, and then, the reaction was carried out under an argon atmosphere at room temperature for 10 days (see [Chem. 10] described below). After completion of the reaction, the reaction solution was added into hexane; and then, a brown solid whereby formed was collected by centrifugal separation, and then dissolved into small amount of chloroform. Thereafter, the solid was reprecipitated by addition of hexane. After washing with ether, it was dried under vacuum at room temperature overnight (yield of 1587 mg and 82%).

[Chem. 10]

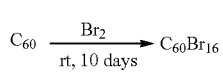

Figure 11:
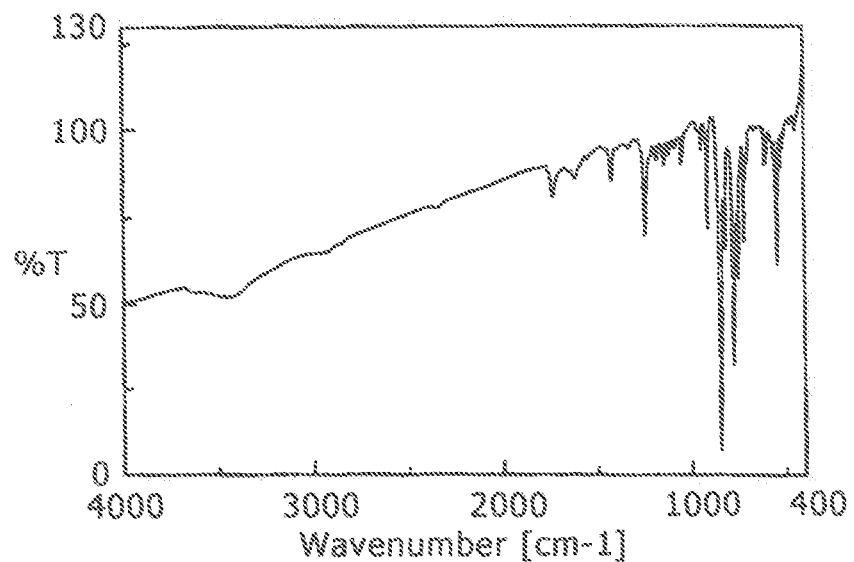
FIG. 11 is a FT-IR spectrum chart of brominated fullerene $C_{60}Br_{16}$.

IR spectrum of the product is shown in FIG. 11. IR spectrum of FIG. 11 shows a large and sharp C—Br stretching and vibration peak at 848 cm$^{-1}$ and resembles well with the IR spectra of brominated fullerenes $C_{60}Br_8$ and $C_{60}Br_{24}$ described in Non-Patent Document 5, thereby showing a basis for the average structure of $C_{60}Br_{16}$. Values of the elemental analysis thereof were: 35.48% for C, 0.45% for H, and 62.47% for Br; and these values coincided well with the calculated values for $C_{60}Br_{16}$ (36.05% for C and 63.95% for Br).

Synthesis of Partially Brominated, Hydroxylated Fullerene $C_{60}Br_{4.5}(OH)_9 \cdot 4H_2O$ $C_{60}Br_{16}$ (50 mg) obtained along the line described above was added with an aqueous sodium hydroxide (20.0 mM, 10 mL) that was prepared so as to give concentration of 8 equivalents relative to the fullerene nucleus therein, and then dispersed into water by irradiation with an ultrasonic wave; and then, the reaction was carried out at 60° C. for 30 minutes (see [Chem. 11] described below). After confirming that the solution thereof became neutral by using a pH-test paper, a brown solid which was precipitated out by addition of hexane, diethyl ether, and 2-propanol with the ratio of 5:6:7 relative to water volume was collected by centrifugal separation. After washing with ether, this was dried under vacuum at room temperature overnight (yield of 32.4 mg and 99%).

[Chem. 11]

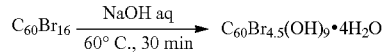

Figure 12:
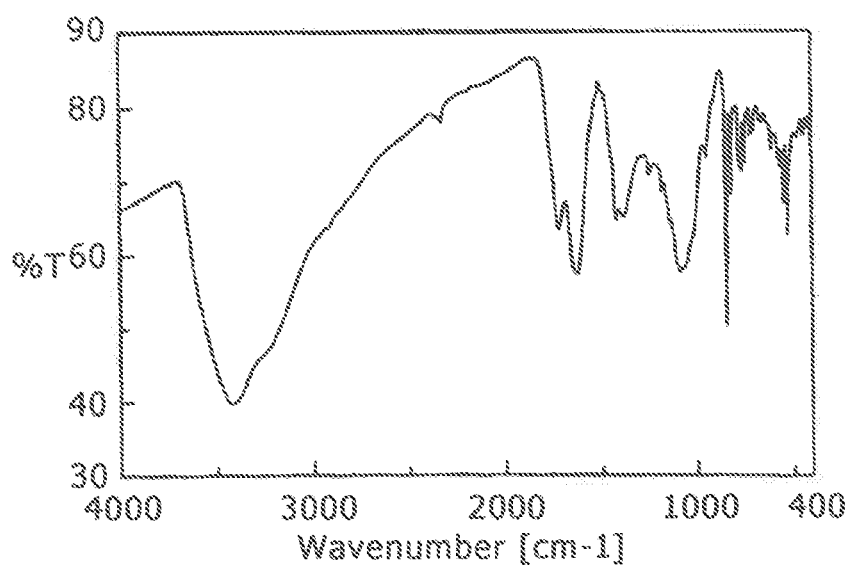
FIG. 12 is a FT-IR spectrum chart of partially brominated, hydroxylated fullerene $C_{60}Br_{4.5}(OH)_9 \cdot 4H_2O$.

IR spectrum of this product is shown in FIG. 12. The IR spectrum of FIG. 12 is significantly different from the spectrum (see FIG. 11) of brominated fullerene $C_{60}Br_{16}$ which was used as the starting raw material thereof, suggesting that the reaction took place, and at the same time, showing spectrum characteristics of both of the hydroxylated fullerene and the brominated fullerene. In addition, in a thermogravimetric analysis thereof, weight loss of 5.0 wt % was observed while heating from room temperature to around 100° C., whereby this weight loss was estimated as amount of the secondary bound water contained in the product. Values of the elemental analysis thereof were: 55.26% for C, 1.43% for H, and 27.12% for Br; and these values coincided well with the calculated values for $C_{60}Br_{4.5}(OH)_9 \cdot 4H_2O$ (55.21% for C, 1.31% for H, 27.55% for Br, and 5.5% by weight for $H_2O$).

Test Example 1

Function Test of the Sample to Cedar Pollen Allergen (Cry j1)

A 1% (by weight/volume) sample solution was prepared from each of the compounds synthesized in Examples 1 to 5, an allergen (Cry j1) dissolved into a phosphate buffer solution was added into the sample solution so as to give 100 ng/mL of the concentration thereof, and then, they were mixed by using a vortex; thereafter, reaction was carried out with shaking the mixture at 4° C. The solution was recovered at the respective predetermined intervals (after 5 minutes and 30 minutes); and a supernatant thereof after centrifugal separation was analyzed as to the allergen concentration (A) by using a sandwich ELISA method (Enzyme-Linked Immunosorbent Assay). As a comparison, by using the concentration (B) of an allergen solution which did not have the fullerene sample added thereto, the allergen reduction rate (%) was obtained from the following equation.

Reduction rate (%)=$(B-A)/B \times 100$

Specific procedure of the sandwich ELISA method will now be described. Anti-Cry j1 antibody is immobilized in each well of a microplate; and after cleaning it, post coating thereof is conducted. After further cleaning, a sample solution or a standard allergen solution is added thereinto to carry out a primary reaction. After cleaning thereof, an anti-Cry j1 biotin-labeled antibody is added thereinto to carry out a secondary reaction. After further cleaning thereof, an enzyme reagent streptavidin HRP is added thereinto; and after cleaning thereof, an o-phenylenedimaine substrate is added thereinto to carry out a chromogenic reaction. After termination of the reaction by adding dilute sulfuric acid, absorbance at the wavelength of 490 nm is measured by using a microplate reader. From a calibration curve predetermined by using the standard allergen solution, allergen concentration in each sample solution is obtained.

Figure 13:
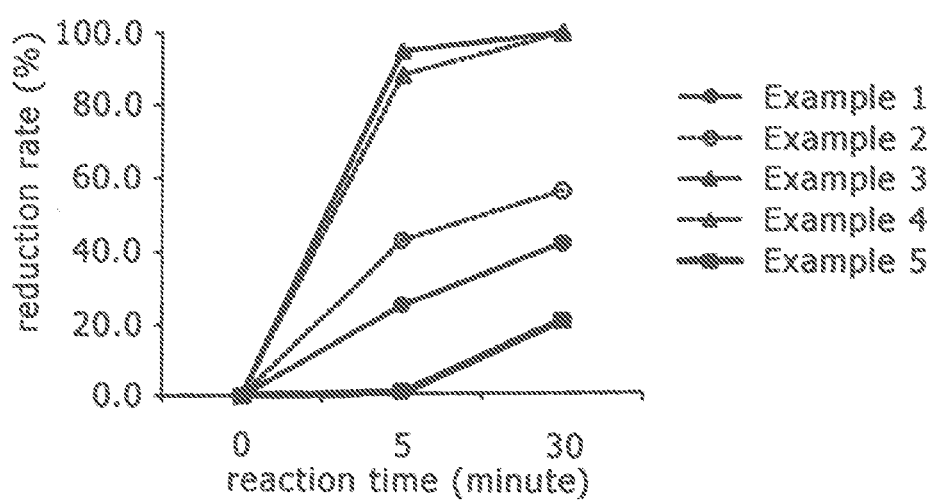
FIG. 13 is a diagram showing an allergen reduction rate at each reaction time.

The results thereof are shown in FIG. 13. In any of five samples, allergen concentration in the solution was decreased, with the decrease of the allergen concentration being larger with passage of the time. Especially in the samples of Example 3 and Example 4, strong adsorbing effect of the allergen in a short time was observed, as can be seen the reduction rate of 90% at 5 minutes and 99% or more at 30 minutes.

Comparative Example 1

By using the hydroxylated fullerene $C_{60}(OH)_{44} \cdot 8H_2O$ synthesized in Example 1, the allergen adsorbing test identical to that of Test Example 1 was carried out with the conditions similar to those of Test Example 1. As a result, the reduction rate remained at 6.2% even after 60 minutes.

INDUSTRIAL APPLICABILITY

The fullerene derivative of the present invention has a function of an anti-allergen and an anti-virus; and thus, it can be used in products of a mask and a filter.

In addition, the fullerene derivative of the present invention has an amphipathic property of both hydrophilicity and hydrophobicity; and thus, it can be applied, impregnated, or chemically bonded to surface of various materials. Accordingly, it has a potential of being applicable in a novel organic synthesis, a polymer modification, a surface modification, a medical field, and so on.

What is claimed is:

1. A partially halogenated, hydroxylated fullerene of the following general formula of $C_pX_n(OH)_m$, characterized in that the partially halogenated, hydroxylated fullerene has a halogen group and a hydroxyl group at a ratio of 1:71 to 1:1 (halogen group:hydroxyl group), $$C_pX_n(OH)_m$$

wherein p represents an even number of 60 or more,
X represents a halogen group,
n represents a number of more than 0 and up to 48, and
m represents a number of more than 9 and up to 44.

2. An allergen adsorbent comprising a partially halogenated, hydroxylated fullerene of the following general formula of $C_pX_n(OH)_m$, characterized in that the partially halogenated, hydroxylated fullerene has a halogen group and a hydroxyl group at a ratio of 1:71 to 1:1 (halogen group:hydroxyl group), $$C_pX_n(OH)_m$$

wherein p represents an even number of 60 or more,
X represents a halogen group,
n represents a number of more than 0 and up to 48, and
m represents a number of more than 9 and up to 44.

* * * * *